(12) United States Patent
Tuma et al.

(10) Patent No.: US 9,907,623 B2
(45) Date of Patent: Mar. 6, 2018

(54) GENERATING IMAGES FOR AT LEAST TWO DISPLAYS IN IMAGE-GUIDED SURGERY

(71) Applicant: Brainlab AG, Munich (DE)

(72) Inventors: Gregor Tuma, Munich (DE); Markus Bartenstein, Munich (DE); Johannes Manus, Munich (DE); Michael Gschwandtner, Munich (DE); Fritz Vollmer, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/623,312

(22) Filed: Jun. 14, 2017

(65) Prior Publication Data

US 2017/0281285 A1    Oct. 5, 2017

Related U.S. Application Data

(60) Continuation of application No. 15/381,990, filed on Dec. 16, 2016, now Pat. No. 9,775,684, which is a
(Continued)

(51) Int. Cl.
| | |
|---|---|
| *A61B 90/00* | (2016.01) |
| *A61B 34/00* | (2016.01) |
| *G06F 3/14* | (2006.01) |
| *G09G 5/00* | (2006.01) |
| *A61B 34/20* | (2016.01) |

(Continued)

(52) U.S. Cl.
CPC .............. *A61B 90/37* (2016.02); *A61B 34/20* (2016.02); *A61B 34/25* (2016.02); *G06F 3/1423* (2013.01); *G09G 5/003* (2013.01); *G09G 5/32* (2013.01); *A61B 2090/372* (2016.02); *G06F 3/0488* (2013.01); *G09G 2300/04* (2013.01); *G09G 2380/08* (2013.01)

(58) Field of Classification Search
CPC ......... A61B 90/37; A61B 34/20; A61B 34/25; A61B 2090/372; G06F 3/1423; G06F 3/0488; G09G 5/003; G09G 5/32; G09G 2300/04; G09G 2380/08
See application file for complete search history.

(56) References Cited

U.S. PATENT DOCUMENTS

| | | |
|---|---|---|
| 7,371,177 B2 | 5/2008 | Ellis et al. |
| 7,453,418 B2 | 11/2008 | Palmquist |

(Continued)

FOREIGN PATENT DOCUMENTS

| | | |
|---|---|---|
| EP | 2119413 A1 | 11/2009 |
| WO | 2005065180 A2 | 7/2005 |

OTHER PUBLICATIONS

European Patent Office, Substantive examination for EP application No. 10728656.9 published as EP2584989, Date of May 1, 2013.
(Continued)

*Primary Examiner* — Dmitriy Bolotin
(74) *Attorney, Agent, or Firm* — Tucker Ellis LLP

(57) ABSTRACT

A system, in particular for image-guided surgery, comprising: at least two display devices; a position determinator for determining the relative position of the display devices; and an image generator for generating images, which are to be displayed by the display devices, in accordance with the determined relative position.

17 Claims, 2 Drawing Sheets

Related U.S. Application Data division of application No. 13/806,361, filed as application No. PCT/EP2010/059140 on Jun. 28, 2010, now abandoned.

(51) Int. Cl.
*G09G 5/32* (2006.01)
*G06F 3/0488* (2013.01)

(56) References Cited

U.S. PATENT DOCUMENTS

| | | |
|---|---|---|
| 8,121,640 B2 | 2/2012 | Russ et al. |
| 8,253,649 B2 | 8/2012 | Imai et al. |
| 8,310,468 B2 | 11/2012 | Martin |
| 8,462,103 B1 | 6/2013 | Moscovitch et al. |
| 8,830,264 B2 | 9/2014 | Son et al. |
| 2003/0107586 A1 | 6/2003 | Takiguchi et al. |
| 2003/0151562 A1 | 8/2003 | Kulas |
| 2004/0125044 A1 | 7/2004 | Suzuki |
| 2004/0263424 A1 | 12/2004 | Okuley |
| 2005/0020909 A1 | 1/2005 | Moctezuma de la Barrera et al. |
| 2005/0168399 A1 | 8/2005 | Palmquist |
| 2006/0002258 A1 | 1/2006 | Nakamura et al. |
| 2006/0071135 A1 | 4/2006 | Trovato |
| 2006/0082518 A1 | 4/2006 | Ram |
| 2007/0019936 A1 | 1/2007 | Birkenbach et al. |
| 2007/0038059 A1 | 2/2007 | Sheffer et al. |
| 2007/0106128 A1 | 5/2007 | Lavallee |
| 2008/0106374 A1 | 5/2008 | Sharbaugh |
| 2009/0161302 A1 | 6/2009 | Ferren et al. |
| 2009/0248036 A1 | 10/2009 | Hoffman et al. |
| 2009/0326318 A1 | 12/2009 | Tognaccini et al. |
| 2010/0053164 A1 | 4/2010 | Imai et al. |
| 2010/0312833 A1 | 12/2010 | Rimmer et al. |
| 2012/0326945 A1* | 12/2012 | Ellis ............ G06F 3/1423 345/1.1 |
| 2013/0093738 A1 | 4/2013 | Manus |
| 2015/0227224 A1* | 8/2015 | Park ............ G06F 3/0487 345/173 |

OTHER PUBLICATIONS

European Patent Office, International Preliminary Report on Patentability for PCT/EP2010/059140 issuance of report dated Dec. 28, 2012.

Maier, C., European Search Report with Examination for corresponding EP divisional application EP17174884, 8 pages, date of completion Nov. 7, 2017, Munich, Germany.

* cited by examiner

GENERATING IMAGES FOR AT LEAST TWO DISPLAYS IN IMAGE-GUIDED SURGERY

CROSS REFERENCE TO RELATED APPLICATIONS

This application is a continuation of U.S. patent application Ser. No. 15/381,990, filed on Dec. 16, 2016, which is a divisional of U.S. patent application Ser. No. 13/806,361 filed Dec. 21, 2012 (now abandoned) which is the U.S. National Stage of International Application No. PCT/EP2010/059140 filed Jun. 28, 2010, the entire contents of each of which are incorporated herein by reference.

TECHNICAL FIELD

The present invention relates to a system which is in particular for displaying images, in particular in the medical field, in particular for image-guided surgery, comprising at least two display devices, and to a method for generating images to be displayed by the display devices.

BACKGROUND

Systems for image-guided surgery are known and commercially available. Such systems comprise at least one display device, such as a monitor or a screen, for displaying information which aids the surgeon during surgery. Some of these systems comprise two display devices. The present invention relates to generating images to be displayed by such display devices.

The present invention is directed to a system, in particular for image-guided surgery, comprising at least one and in particular at least two display devices. In particular, the system comprises a position determinator for determining the position, in particular the relative position, of the display device(s). In particular, the system also comprises an image generator for generating images, which are to be displayed by the display device(s), in accordance with the determined position, in particular the relative position. Generating images in accordance with the determined position means that the generated images depend on the determined position. This means in particular that the image generator is capable of generating independent images for each of the display devices.

The image generator can for example generate the same image for all the display devices, the same image for some of the image devices while the other display devices display different images, or a different image for each display device. In particular, the decision as to which image is to be generated for a particular display device depends on the position, in particular the relative position, of the display devices. If more than two display devices are provided, the term "relative position" comprises a set of relative positions which comprises at least one position of each of the display devices relative to another of the display devices.

In this document, the term "position" means a combination of location and alignment. The location means the point in space at which an object is located in up to three spatial or translational dimensions. The alignment or orientation means the rotational angle at which an object is positioned in up to three rotational dimensions. The term "relative position" means the relative spatial and/or rotational displacement, each in up to three dimensions, of two objects such as display devices. The relative position between two objects can be determined either directly or indirectly. Indirectly determining it means for example determining the positions of two objects relative to a common reference and determining the relative position between the objects from the relative positions of the objects and the reference.

In accordance with the invention, a method of generating images for at least one and in particular at least two display devices (for instance, in a system for image-guided surgery) comprises the steps of determining the position, in particular the relative position, of the display device(s) and generating images, which are to be displayed by the display device(s), in accordance with the determined position, in particular the relative position.

In this document, the expression "observing a display device" means observing the image displayed by the display device, hence if a person can see, view or observe a display device, this means that this person can see, view or observe the image displayed by the display device.

In one arrangement, a viewer can see several or all of the display devices. In this case, it is advantageous to display different images on each of the display devices which can be seen. An enlarged view of an object or a graphical user interface of an application is for example spread over several display devices. In another example, graphical user interfaces of multiple applications are spread over several display devices. It is of course also possible to duplicate the same image on several display devices.

In another configuration, each display device or subgroup of display devices can be viewed by a different person or group of persons. In this case, the preferred scenario is to duplicate the same image on several display devices. It is also of course still possible to generate different images for the display devices, for example if different persons are to be provided with different information.

In the present invention, the content displayed on at least two display devices, i.e. exactly two or more than two (for instance, three or four) display devices, is automatically adjusted in accordance with the relative position of the display devices. An image displayed on one display device is for example enlarged and displayed on two or more display devices if one or more other display devices are placed next to the first display device at a distance which is less than a threshold value. If the distance between the first display device and another display device(s) is increased above the threshold value, then the image is no longer displayed in the enlargement and another image, such as the graphical user interface of an application, is displayed on the other display device.

In one embodiment, the system comprises an adjustable mounting for a display device, the mounting consisting of multiple elements, wherein two adjoining elements are connected via an adjustable joint. Typical examples of such mountings are arms or carrier arms. The system also comprises at least one sensor for detecting the state of at least one joint. Preferably, one sensor is provided for each joint. The state of a joint represents the relative position of the elements connected by said joint. If the joint is a pivot bearing, then the sensor output is an angle. If the joint is a bearing which allows a translational movement, then the sensor output is a distance. The position determinator can calculate the position of the display device, in particular the relative position of the display device relative to a reference such as the base of a mounting, from the states of all the joints of the mounting and the structure of the mounting. If this information is known for more than one display device, then the relative position of these display devices can be determined. In general, the relative position is determined from the state of at least one joint which connects adjoining elements of a mounting device for a display device.

In another embodiment, a marker device is attached to at least one display device, wherein the position determinator is configured to determine the relative position from the position of the marker device. In terms of a method, the relative position is determined from the positions of marker devices attached to the display devices. The position determinator can determine the relative position of the display devices from the relative position of the marker devices attached to the display devices and the known relative positions of the display devices and the respectively attached marker devices.

A marker device can for example be a reference star or a pointer or one or more (individual) markers which are in a predetermined spatial relationship. This predetermined spatial relationship is in particular known to a navigation system and for example stored in a computer of the navigation system.

It is the function of a marker to be detected by a marker detection device (for example, a camera or an ultrasound receiver), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic-shape.

In another embodiment, the system comprises at least one camera which observe(s) the display devices, wherein the position determinator is configured to determine the relative position from the output image of the at least one camera. In terms of the method, the relative position is determined from at least one output image of at least one camera, wherein the output image shows the display devices. The camera captures an image which shows the display devices. The relative position of the display devices can be calculated using image analysis. Preferably, all the display devices are within the field of view of a camera. Alternatively, different display devices can be observed by different cameras. The relative position of the display devices can then be determined from the output images of multiple cameras. The camera can be a 2D camera or a stereoscopic camera, such as for example a stereoscopic camera of a medical navigation system. A stereoscopic camera can also be used as a marker detection device.

In another embodiment of the present invention, the system comprises a camera which is attached to a display device, wherein the position determinator is configured to determine the relative position from the output image of the camera. In terms of the method, the relative position is determined from at least one output image of a camera which is attached to a display device. Such a camera observes the surroundings of the display device. The position of the camera can be calculated using image analysis. In one example, a 3D model of the surroundings is provided to a position determinator, and a virtual image is rendered for a virtual location and a virtual perspective, i.e. a virtual camera position. If the rendered image matches the camera output image, then the position of the camera matches the virtual position.

Using the camera which is attached to the display device, it is possible to detect incident light upon the camera, and therefore incident light upon the display device. Unwanted reflections of the incident light can be determined from the detection result. The effects of these reflections can be reduced by adapting the displayed image and/or by repositioning the display device. In general, any other device which is suited to detect electromagnetic waves in the visual spectrum can be used instead of a camera. In particular, a device or multitude of such devices, each receiving waves from a defined solid angle, can be used. An example for such a device is a photo detector or photo resistor provided with a lens defining a solid angle from which incident light is detected.

In another embodiment according to this invention or an additional invention, the system comprises at least one or at least two display devices and a viewer detector, such as an RFID reader or camera, for detecting a viewer who is viewing a display device, wherein the image generator is configured to generate an image for this display device in accordance with the determined viewer. In this embodiment, the position determining means is optional. A viewer detector can be configured and positioned to determine the viewer or viewers of one or more display devices. In a preferred embodiment, there is a dedicated viewer detector assigned to each display device for which the viewer is to be detected. In terms of the method, a viewer who is viewing a display device is determined, and the image to be displayed by this display device is generated in accordance with the determined viewer. In general, a viewer who is viewing one, two or more than two display devices can be identified, and/or one or more viewers of a display device can be identified.

Each potential viewer for example carries an RFID chip having a unique ID which can be read out by the RFID reader. The viewer who is viewing the display device is thus identified. In particular, a directed antenna is used to detect RFID chips only in the area from which the corresponding display device can be viewed. Additionally or alternatively, a camera—for example, a camera which is attached to a display device—captures an image of the viewer, and the viewer is then identified by image analysis, for example by comparing the image of the viewer with reference images which are in particular stored in a reference image database or by face recognition. In face recognition, a possible approach is to detect individual facial components and/or features of the person to be identified, such as the distance between the eyes or the distance between an eye and the nose, and so on.

Once the viewer has been determined, the image generator generates one or more images which are adapted to the needs of the determined viewer who is viewing the display device or display devices. For example, the display device or devices being viewed by a surgeon can then show information for navigating a medical instrument or can show medical images such as x-ray, CT or MRI images, while the display device or devices being viewed by other operating room personnel can show medical information such as the heart rate or pulse of the patient or an image of a microscope. In addition to image generation depending on the viewer, or as an alternative, it is possible to configure a touch screen functionality depending on the identified viewer. For example, the touch screen functionality is only provided to a person or group of persons which is allowed to input or amend data. In general, the touch screen functionality of a display device can be enabled, disabled or configured depending on the detected viewer, in particular in combination with the generation of the graphical user interface.

As an option, eye tracking can be performed on the output image of the camera, in particular in combination with the viewer identification by image analysis. In a particular embodiment, the result of the eye tracking can be used for determining whether or not a person which is in a position from which he or she could view the display device actually does so. If the person could view more than one display devices, it can be determined which of the display devices is actually viewed. Some data can for example always be displayed on the display device which is actually viewed by the viewer.

In a specific embodiment, the system comprises: an adjustable mounting which consists of multiple elements, wherein two adjoining elements are connected via an adjustable joint; and at least one actuator for adjusting the state of at least one joint. Accordingly, the method comprises the step of generating a drive signal for driving at least one actuator in order to adjust the state of at least one joint which connects two adjoining elements of an adjustable mounting which holds a display device. A "drive signal" can also be an instruction to generate a drive signal, in particular if the method is implemented by a software which instructs a suitable means to generate the drive signal. The mounting can be adjusted using the actuators, in order to move the corresponding display device to a desired position. This desired position is for example a position in which no reflections occur. As mentioned above, the reflections are for example detected by a camera which is directed towards the display. The images generated by the camera are analyzed for reflections, and the position of the display is varied so as to minimize the reflections. The actuators can also be driven in such a way that the display device follows the movement of a viewer, such that the display device is always positioned such that it can be viewed by the viewer. The position of the viewer can be detected by one or more cameras which can be mounted on the display.

The system in accordance with the invention is in particular a navigation system. A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU), a working memory, advantageously an indicating device for issuing an indication signal (for example a visual indicating device such as a monitor and/or an audio indicating device such as a loudspeaker and/or a tactile indicating device such as a vibrator) and advantageously a permanent data memory, wherein the data processing device processes navigation data forwarded to it by the receiver and can advantageously output guidance information to a user via the indicating device. The navigation data can be stored in the permanent data memory and for example compared with data which have been stored in said memory beforehand.

In one embodiment, at least one of the display devices comprises a touch-sensitive surface. This touch-sensitive surface can exhibit a functionality which depends on the person viewing the display device and/or the relative position of the display devices.

The present invention also relates to a program which, when running on a computer or when loaded onto a computer, causes the computer to perform the method as described above, and/or to a program storage medium on which the program is stored (in particular non-transitory), and/or to a computer on which the program is running or into the memory of which the program is loaded, and/or to a signal wave, in particular a digital signal wave, carrying information which represents the program, wherein the aforementioned program in particular comprises code means which are adapted to perform all the steps of the method as described above.

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

It is within the scope of the present invention to extract one or more features of different embodiments or options to form a new embodiment or to omit features which are not essential to the present invention from an embodiment. In particular, images can be generated in accordance with the identity of the viewer in a system comprising one display device only and/or independently of the relative position between two or more display devices.

BRIEF DESCRIPTION OF THE FIGURES

The present invention shall now be explained in more detail by referring to an example embodiment which is depicted in the attached figures, which show.

DETAILED DESCRIPTION

Figure 1:
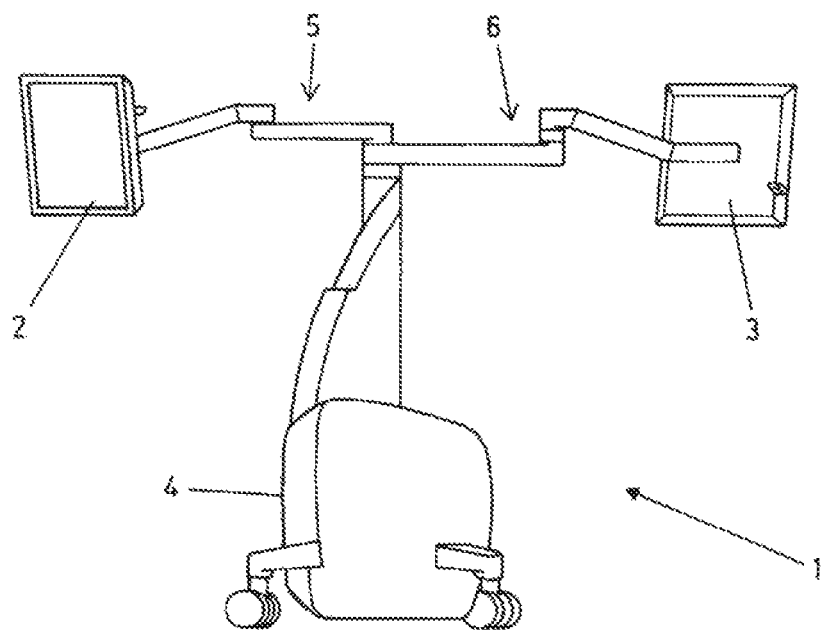
FIG. 1 a system for image-guided surgery, comprising two monitors.

FIG. 1 shows a system 1 which is designed to be used in image-guided surgery. The system 1 comprises two monitors 2 and 3 as example embodiments of display devices. The monitor 2 is attached to a base 4 via an arm 5 which is used as an adjustable mounting. The monitor 3 is attached to the base 4 via an arm 6 which is used as an adjustable mounting. The monitors 2 and 3 can be respectively moved into desired positions using the arms 5 and 6. At all times, the monitors 2 and 3 exhibit a relative position with respect to each other.

Figure 2:
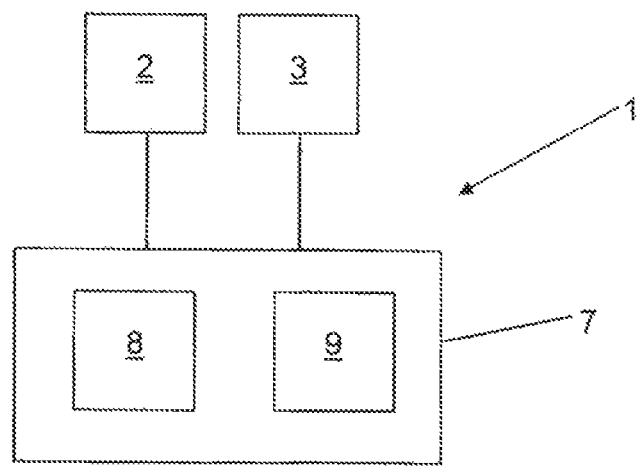
FIG. 2 a schematic block diagram of the system of FIG. 1.

FIG. 2 shows a schematic block diagram of the system 1. The monitors 2 and 3 are connected to a control unit 7. The control unit 7 comprises a position determinator 8 and an image generator 9. The position determinator 8 determines the relative position between the monitors 2 and 3. The image generator 9 generates images which are to be displayed by the monitors 2 and 3. The image generator 9 can generate different images for each monitor or duplicate the same image on two or more monitors, the latter resulting in cloned images.

In general, the position determinator 8 can be configured to determine the relative position between the monitors not directly but rather from the relative position of each monitor as compared to a known reference.

Figure 3:
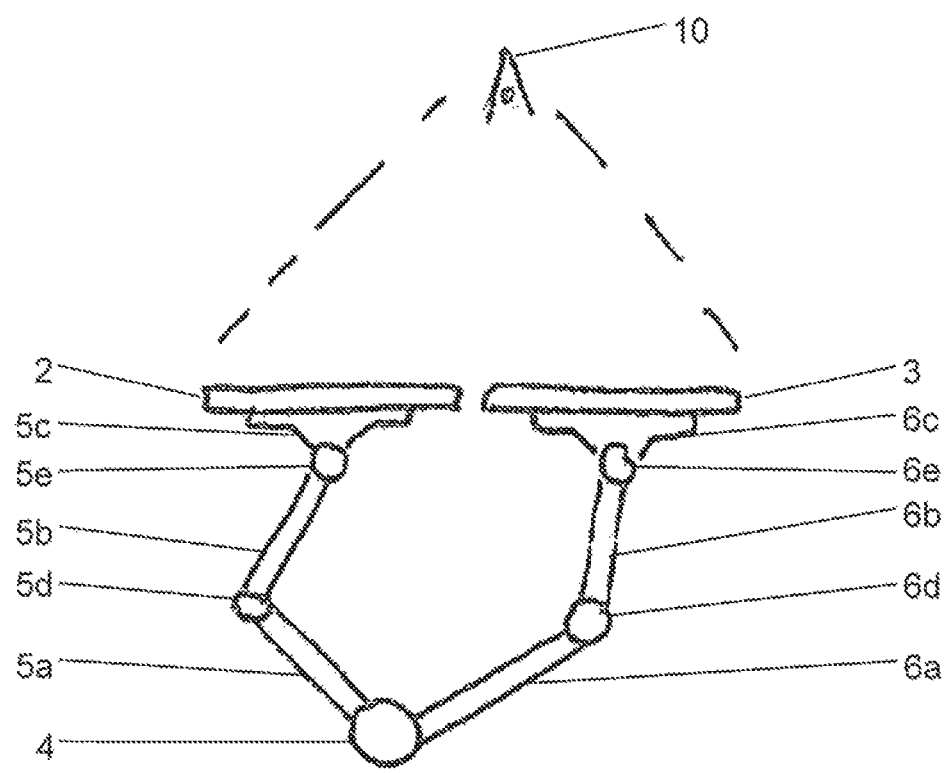
FIG. 3 the system of FIG. 1 in a first schematic scenario.

FIG. 3 shows a first scenario in which a single person 10 or group of persons can see both the monitors 2 and 3. In addition, the arms 5 and 6 are depicted in more detail.

As shown in FIG. 3, the arm 5 basically consists of two elements 5a and 5b and a mounting bracket 5c. The mounting bracket 5c is fixed to the monitor 2 and connected to the element 5b via a ball joint 5e. The ball joint 5e enables a rotational relative movement between the bracket 5c and the element 5b in two dimensions. The elements 5b and 5a are connected via a pivot joint which enables a relative movement between these two elements in one rotational dimension. The element 5a is connected to the base 4 via another pivot joint (not shown).

Similarly, the arm 6 basically consists of two elements 6a and 6b and a mounting bracket 6c. The monitor 3 is affixed to the mounting bracket 6c. The mounting bracket 6c and the element 6b are connected via a ball joint 6e, while the elements 6b and 6a are connected via a pivot joint 6d. The element 6a is also connected to the base 4 via another pivot joint (not shown).

For each joint, i.e. the joints 5d, 5e, 6d, 6e and the two joints between the base 4 and the elements 5a and 6a, respectively, a sensor is provided which determines the current state, i.e. the position, of the respective joint and transmits this state to the position determinator 8. The position determinator 8 can then calculate the relative position between the monitors 2 and 3 from the different states of the joints and the known geometric structure of the arms 5 and 6.

In the present scenario, the position determinator 8 determines that both monitors 2 and 3 can be seen by the person 10, who is for example a surgeon. On the basis of this information, the image generator 9 calculates the images to be displayed by the monitors 2 and 3 and sends the images to the corresponding respective monitors.

In one example, the graphical user interface of a software program is spread over the two monitors 2 and 3. In a second example, the graphical user interface of a first software is displayed on the monitor 2, and a graphical user interface of a second software is displayed on the monitor 3. In a third example, the graphical user interface of a software is displayed on the monitor 2, while medical data such as for example image data generated by an x-ray, CT or MRI imaging apparatus or any other imaging apparatus are displayed on the monitor 3.

In one specific embodiment of the third example or in the general case of two or more adjacent monitors, the previously described distribution across the two monitors 2 and 3 is maintained as long as the distance between the monitors 2 and 3 is above a predefined threshold value, such as for example 5 cm. If the monitors 2 and 3 are brought closer to each other, resulting in a distance which is less than the threshold value, the medical image shown on the monitor 3 is enlarged and spread across the monitors 2 and 3. If the distance between the monitors 2 and 3 is subsequently increased again, the image generator 9 returns to the previous operating mode and displays the graphical user interface on the monitor 2 and the medical data on the monitor 3. In general, if two or more monitors are adjacent and can be seen by the same person, the image generator 9 generates the images to be displayed by these monitors in accordance with the distance between the monitors. Adjacent monitors are in particular monitors which can be viewed by the same person and which are in particular spaced apart by a distance which is smaller than a threshold value, such as for example the image size of a monitor. An alternative or additional criterion for monitors being adjacent is the angle between the display screens of the monitors. If this angle is zero, i.e. the screens are in the same or parallel planes, or below a threshold value, such as 45 degrees, 30 degrees, 20 degrees, 10 degrees or 5 degrees, then the monitors are considered adjacent.

Optionally, the image generator 9 generates an image for a display device in accordance with the relative position between this display device and an object, such as for example a patient or an operating table. This relative position can also be determined by the position determinator 8. Information about the type and location of the surgery, with reference to the patient or operating table, is also optionally provided to the image generator 9, such that the images are also generated in accordance with this information. If a display device is for example positioned such that the surgeon can see the display device, then information relating to the actual surgery is displayed, while general information about the condition of a patient is displayed on a display device which is positioned towards other medical personnel, such as for example a surgical nurse. If, for example, the image generator 9 knows that surgery is being performed on the head of a patient and that a monitor is directed towards a position near the head, then information relevant to the surgeon is displayed. In other words, the person viewing a monitor is identified from the position which the monitor is facing or from which the monitor can be viewed, and from information as to the person or persons who do or may be expected to remain at this position.

Figure 4:
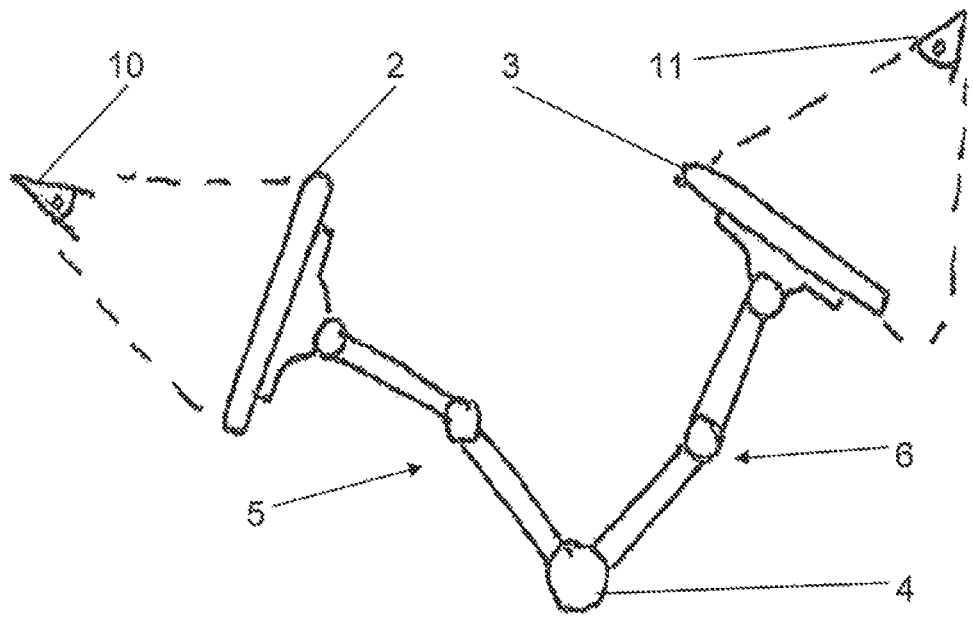
FIG. 4 the system of FIG. 1 in a second schematic scenario.

In the scenario shown in FIG. 4, the monitors 2 and 3 are facing different persons or groups of persons. The monitor 2 is facing the person 10, for example a surgeon, while the monitor 3 is facing a person 11, such as for example a medical nurse or an observer. The position determinator 8 identifies this scenario from the states of the joints of the arms 5 and 6. On the basis of this information, the image generator 9 decides to display the same image, i.e. a duplicated image, on both the monitors 2 and 3. Alternatively, the image generator 9 can be programmed to display different images on the monitors 2 and 3, for example consisting of the same basic image, but supplemented by information which is of particular interest to the person viewing the respective monitor. The image generator 9 can be programmed while the system is being used, for example using an input device (not shown) such as a touch-sensitive surface on one or more of the monitors.

In general, the relative position between a monitor and another object, such as a patient or an operating table, can be determined, for example by the position determinator 8. The images can then be generated by the image generator 9 on the basis of this relative position. In the scenario shown in FIG. 4, the image generator 9 determines that the monitor 2 is facing a position at which the surgeon 10 is expected to be standing, while the monitor 3 is facing away from the patient. From this information, the image generator 9 knows which information to display on which monitor.

As an alternative to or in combination with the information about the relative position between a monitor and another object, the images can also be generated on the basis of information about the identity of a viewer who is viewing the monitor. The viewer can for example reveal his or her identity to the control unit 7 by inputting this information via a keyboard or by swiping a keycard through a reader. The viewer can also be wearing an RFID chip which is read out by an RFID reader. The viewer can also be identified biometrically.

As an alternative to the sensors which detect the states of the joints of the arms 5 and 6, a marker device can be attached to a monitor. A marker detection device (not shown), such as for example a stereoscopic camera of a medical navigation system, detects the positions of the markers and provides this information to the control unit 7. The position determinator 8 then calculates the relative position between the monitors 2 and 3 from the positions of the markers and the known relative position between each marker and the monitor which it is attached to.

In another alternative, one or more cameras (not shown) are provided in a position which is such that each camera observes one or more, preferably all, of the monitors. By analysing the output image or images of the camera or cameras, the position of the monitors can be determined, either relative to a reference or relative to each other.

In yet another alternative, a camera is attached to a monitor. The position of the camera can be determined from the output image of the camera, by image analysis. The relative position between the monitors can be calculated from the known relative position between the monitor and the corresponding camera. In one example, the relative position can be calculated directly if a monitor can be seen in the output image of a camera which is attached to another monitor. In another example, the relative position of the monitors is calculated relative to a reference, and the relative position between the monitors is calculated from the positions of these monitors relative to the reference.

A person who is viewing a monitor can be identified using a camera which is attached to the monitor. When generating the image which is to be displayed on this monitor, the image generator 9 can generate the image in accordance with the identity of the viewer, as explained above.

Incident light onto a monitor can be detected using a camera which is attached to the monitor. The intensity level of the ambient light can be determined from the incident light, in order to adjust the contrast and/or brightness of the monitor and/or of the image being displayed on the monitor. Additionally or alternatively, unwanted reflections of the incident light onto the viewer can be determined. The brightness and/or contrast of the monitor and/or the image can then be adjusted on the basis of this information. The most important data can also be displayed in a region of the image in which the monitor does not produce unwanted reflections. The position of the monitor can also alternatively or additionally be automatically adjusted so as to prevent the reflections, for example using drive actuators (not shown) which adjust the mounting of the monitor.

Actuators of the mounting can additionally or alternatively be used to continuously reposition the monitor to face a moving viewer and/or in order to move the monitor into a desired position, such as an initial position for the surgery. This initial position can be explicitly programmed or can be automatically derived from the type and/or location of the surgery.

The example embodiments which have been described above with reference to the figures are purely illustrational and in no way limit the scope of the present invention as defined in the following claims.

The invention claimed is:

1. A system for use in an associated image-guided procedure, the system comprising:
   a first display device;
   a second display device;
   a position determinator, the position determinator determining a relative position between the first and second display devices;
   an image generator, the image generator being configured to generate a first image to be displayed by the first display device in accordance with the determined relative position between the first and second display devices, and the image generator being configured to generate a second image to be displayed by the second display device in accordance with the determined relative position between the first and second display devices; and
   a viewer detector, the viewer detector detecting an associated person viewing at least one of the first display device and/or the second display device, and the viewer detector identifying the associated person who is viewing the at least one of the first and/or second display devices as an identified viewer,
   wherein the image generator generates in accordance with the identified viewer at least one of a particular first image and/or a particular second image for the at least one of the first and/or second display devices being viewed by the associated person, respectively.

2. The system according to claim 1, further comprising:
   a first adjustable mounting supporting the first display device relative to an associated base, the first adjustable mounting comprising a plurality of first support elements mutually connected via a set of first adjustable joints;
   a second adjustable mounting supporting the second display device relative to the associated base, the second adjustable mounting comprising a plurality of second support elements mutually connected via a set of second adjustable joints; and
   at least one sensor operably connected with the position determinator, the at least one sensor detecting a state of at least one of the first and/or second adjustable mountings, wherein the position determinator determines the relative position between the first and second display devices in accordance with the state of the at least one of the first and/or second adjustable mountings detected by the at least one sensor.

3. The system according to claim 2, wherein:
the at least one sensor detects the state of the at least one of the first and/or second adjustable mountings by detecting a state of one or more of the set of first adjustable joints and/or one or more of the set of second adjustable joints,
the position determinator determines the relative position between the first and second display devices in accordance with the state of the one or more of the set of first adjustable joints and/or one or more of the set of second adjustable joints detected by the at least one sensor.

4. The system according to claim 1, further comprising:
a marker device operatively coupled with at least one of the first and/or second display devices,
wherein the position determinator is configured to determine the relative position between the first and second display devices in accordance with a determined position of the marker device.

5. The system according to claim 1, further comprising:
at least one camera adapted to observe at least one of the first and/or second display devices, and to generate an output image of the observed at least one of the first and/or second display devices,
wherein the position determinator is configured to determine the relative position between the first and second display devices in accordance with the output image of the observed at least one of the first and/or second display devices generated by the at least one camera.

6. The system according to claim 1, further comprising:
a camera operatively coupled with at least one of the first and/or second display devices, the camera being adapted to generate an output image of an observed field of view of the camera,
wherein the position determinator determines the relative position between the first and second display devices in accordance with the output image of the observed field of view of the camera generated by the camera.

7. The system according to claim 1, further comprising:
a first adjustable mounting supporting the first display device relative to an associated base, the first adjustable mounting comprising a plurality of first support elements mutually connected via one or more first adjustable joints;
a second adjustable mounting supporting the second display device relative to the associated base, the second adjustable mounting comprising a plurality of second support elements mutually connected via one or more second adjustable joints; and
at least one actuator, the at least one actuator being operative to adjust a state and/or position of at least one of the first and/or second adjustable joints.

8. The system according to claim 1, wherein:
the second display device is different than the first display device; and
the second image to be displayed by the second display device is different than the first image to be displayed by the first display device.

9. The system according to claim 1, wherein:
wherein the image generator generates the at least one of the particular first image and/or the particular second image for the at least one of the first and/or second display devices being viewed by the associated person in accordance with:
the identified viewer; and
the determined relative position between the first and second display devices.

10. A method of generating images developed in an associated image-guided procedure for first and second display devices of an associated system, the method comprising:
determining by a position determinator of the associated system a relative position between the first and second display devices;
generating by an image generator of the associated system a first image to be displayed by the first display device of the associated system in accordance with the determined relative position between the first and second display devices, and a second image to be displayed by the second display device of the associated system in accordance with the determined relative position between the first and second display devices;
detecting by a viewer detector of the associated system an associated person viewing at least one of the first display device and/or the second display device;
identifying by the viewer detector the associated person who is viewing the at least one of the first and/or second display devices as an identified viewer; and
generating by the image generator in accordance with the identified viewer at least one of a particular first image and/or a particular second image for the at least one of the first and/or second display devices being viewed by the associated person, respectively.

11. The method according to claim 10, further comprising:
detecting, by at least one sensor operably connected with the position determinator, a state of a first adjustable mounting supporting the first display device relative to an associated base and/or a second adjustable mounting supporting the second display device relative to the associated base, the first adjustable mounting comprising a plurality of first support elements mutually connected via a set of first adjustable joints, the second adjustable mounting comprising a plurality of second support elements mutually connected via a set of second adjustable joints; and
determining by the position determinator the relative position between the first and second display devices in accordance with the state of the at least one of the first and/or second adjustable mountings detected by the at least one sensor.

12. The method according to claim 11, further comprising:
detecting, by the at least one sensor, the state of the at least one of the first and/or second adjustable mountings by detecting a state of one or more of the set of first adjustable joints and/or one or more of the set of second adjustable joints; and
determining, by the position determinator, the relative position between the first and second display devices in accordance with the state of the one or more of the set of first adjustable joints and/or one or more of the set of second adjustable joints detected by the at least one sensor.

13. The method according to claim 10, further comprising:
determining by the position determinator the relative position between the first and second display devices in accordance with a determined position of a marker device operatively coupled with at least one of the first and/or second display devices.

14. The method according to claim 10, further comprising:
observing by at least one associated camera at least one of the first and/or second display devices;
generating by the at least one associated camera an output image of the observed at least one of the first and/or second display devices; and
determining by the position determinator the relative position between the first and second display devices in accordance with the output image generated by the associated at least one camera.

15. The method according to claim 10, further comprising:
observing by an associated camera a field of view of the associated camera;
generating by the associated camera an output image of the field of view of the associated camera; and
determining by the position determinator the relative position between the first and second display devices in accordance with the output image generated by the associated camera.

16. The method according to claim 10, further comprising:
generating a drive signal, the drive signal driving at least one associated actuator for adjusting a state of at least one of first adjustable joints mutually connecting a plurality of first support elements comprising a first adjustable mounting supporting the first display device relative to an associated base and/or second adjustable joints mutually connecting a plurality of second support elements comprising a second adjustable mounting supporting the second display device relative to the associated base.

17. The method according to claim 10, wherein the generating the at least one of the particular first and/or second images comprises:
generating by the image generator the least one of the particular first image and/or the particular second image for the at least one of the first and/or second display devices being viewed by the associated person in accordance with:
the identified viewer; and
the determined relative position between the first and second display devices.

* * * * *